US00PP19626P2

(12) United States Plant Patent
Miedema-Jorna

(10) Patent No.: US PP19,626 P2
(45) Date of Patent: Jan. 20, 2009

(54) ***CALIBRACHOA* PLANT NAMED 'FILINDURA PINK'**

(50) Latin Name: ***Calibrachoa* sp.**
Varietal Denomination: Filindura Pink

(75) Inventor: Anita Miedema-Jorna, De Lier (NL)

(73) Assignee: Fides B.V., Tokyo (JP)

( * ) Notice: Subject to any disclaimer, the term of this patent is extended or adjusted under 35 U.S.C. 154(b) by 0 days.

(21) Appl. No.: 12/012,478

(22) Filed: Jan. 31, 2008

(51) Int. Cl.
*A01H 5/00* (2006.01)

(52) U.S. Cl. ..... Plt./413
(58) Field of Classification Search ..... Plt./413
See application file for complete search history.

*Primary Examiner*—Kent L. Bell
*Assistant Examiner*—Georgia Helmer
(74) *Attorney, Agent, or Firm*—C. A. Whealy

(57) ABSTRACT

A new and distinct variety of *Calibrachoa* plant named 'Filindura Pink', characterized by its upright to spreading growth habit; freely branching habit; freely flowering habit; relatively large red purple-colored flowers; and good garden performance.

1 Drawing Sheet

Botanical designation: *Calibrachoa* sp.
Cultivar denomination: 'Filindura Pink'.

BACKGROUND OF THE INVENTION

The present invention relates to a new and distinct cultivar of *Calibrachoa*, botanically known as *Calibrachoa* sp. and hereinafter referred to by the name 'Filindura Pink'.

The new *Calibrachoa* is a product of a planned breeding program conducted by the Inventor in De Lier, The Netherlands. The objective of the breeding program is to create new freely-branching *Calibrachoa* cultivars with compact plant habit, freely flowering habit, and attractive flower color.

The new *Calibrachoa* originated from a cross-pollination made by the Inventor in 2002 in De Lier, The Netherlands of two unnamed proprietary selections of *Calibrachoa* sp., not patented. The new *Calibrachoa* was discovered and selected by the Inventor as a single flowering plant within the progeny of the stated cross-pollination in a controlled environment in De Lier, The Netherlands.

Asexual reproduction of the new *Calibrachoa* by vegetative cuttings in a controlled environment in De Lier, The Netherlands since 2003, has shown that the unique features of this new *Calibrachoa* are stable and reproduced true to type in successive generations.

SUMMARY OF THE INVENTION

The cultivar Filindura Pink has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Filindura Pink'. These characteristics in combination distinguish 'Filindura Pink 'as a new and distinct cultivar of *Calibrachoa:*

1. Upright to spreading growth habit.
2. Freely branching habit.
3. Freely flowering habit.

4. Relatively large red purple-colored flowers.
5. Good garden performance.

Plants of the new *Calibrachoa* can be compared to plants of the parent selections. Plants of the new *Calibrachoa* differ primarily from plants of the parent selections in plant and flowering habit as plants of the new *Calibrachoa* are more uniform and are more freely flowering than plants of the parent selections.

Plants of the new *Calibrachoa* can be compared to plants of the cultivar Super Bell Purplepink, not patented. In side-by-side comparisons conducted in De Lier, The Netherlands, plants of the new *Calibrachoa* differed from plants of the cultivar Super Bell Purplepink in the following characteristics:

1. Plants of the new *Calibrachoa* and the cultivar Super Bell Purplepink differed in stem color.
2. Plants of the new *Calibrachoa* had darker green-colored leaves than plants of the cultivar Super Bell Purplepink.

BRIEF DESCRIPTION OF THE PHOTOGRAPH

The accompanying colored photograph illustrates the overall appearance of the new *Calibrachoa*, showing the colors as true as it is reasonably possible to obtain in colored reproductions of this type. Colors in the photograph may differ slightly from the color values cited in the detailed botanical description which accurately describe the colors of the new *Calibrachoa*. The photograph comprises a side perspective view of a typical flowering plant of 'Filindura Pink' grown in a container.

DETAILED BOTANICAL DESCRIPTION

The aforementioned photograph and following observations, measurements and values describe plants grown in De Lier, The Netherlands, under commercial practice during the spring in glass-covered greenhouse with day and night temperatures averaging 16° C. Rooted young plants had been growing for about ten weeks when the photograph and description were taken. Plants used for the description were grown in 10.5-cm containers. In the following description, color references are made to The Royal Horticultural Society Colour Chart, 1995 Edition, except where general terms of ordinary dictionary significance are used.

Botanical classification: *Calibrachoa* sp. cultivar Filindura Pink.

Parentage:

*Female, or seed, parent*.—Unnamed proprietary selection of *Calibrachoa* sp., not patented.

*Male, or pollen, parent*.—Unnamed proprietary selection of *Calibrachoa* sp., not patented.

Propagation:

*Type*.—By vegetative cuttings.

*Time to initiate roots, summer*.—About five to seven days at temperatures of 19° C. to 20° C.

*Time to initiate roots, winter*.—About six to eight days at temperatures of 19° C. to 20° C.

*Time to produce a rooted young plant, summer*.—About 14 to 19 days at temperatures of 19° C. to 20° C.

*Time to produce a rooted young plant, winter*.—About 14 to 21 days at temperatures of 19° C. to 20° C.

*Root description*.—Fine; white in color.

*Rooting habit*.—Freely branching; moderately dense.

Plant description:

*Plant and growth habit*.—Upright to outwardly spreading plant habit; vigorous growth habit. Freely branching habit with about eight primary lateral branches each with multiple secondary lateral branches; pinching is typically not required.

*Plant height*.—About 32 cm.

*Plant diameter*.—About 48 cm.

Lateral branch description:

*Length*.—About 25 cm.

*Diameter*.—About 1.5 mm.

*Internode length*.—About 1.2 cm.

*Strength*.—Moderately strong.

*Aspect*.—Initially upright to outwardly spreading.

*Texture*.—Densely pubescent.

*Color*.—145B.

Foliage description:

*Arrangement*.—Alternate, simple sessile.

*Length*.—About 3 cm.

*Width*.—About 1.6 cm.

*Shape*.—Oblanceolate.

*Apex*.—Obtuse.

*Base*.—Attenuate.

*Margin*.—Entire.

*Texture, upper and lower surfaces*.—Densely pubescent.

*Venation pattern*.—Pinnate; arcuate.

*Color*.—Developing foliage, upper and lower surfaces: 138A. Fully expanded foliage, upper surface: 137A; venation, 137A. Fully expanded foliage, lower surface: 138A to 138B; venation 138A to 138B.

Flower description:

*Flower arrangement and habit*.—Relatiavely large salverform flowers arranged singly arising from leaf axils. Freely flowering habit with usually 50 open flowers and flower buds developing per plant. Flowers not persistent. Flowers face upright to outwardly.

*Fragrance*.—None detected.

*Natural flowring season*.—Plants flower continuously from the spring throughout the summer in The Netherlands. Plants begin flowering about seven weeks after planting rooted cuttings. Flowers not persistent.

*Flower longevity*.—Individual flowers last about five days on the plant.

*Flower diameter*.—About 3.6 cm.

*Flower depth(height)*.—About 2.8 cm.

*Flower bud*.—Shape: Narrowly oblanceolate. Length: About 1.1 cm. Diameter: About 3 mm. Color: Close to 144A.

*Corolla*.—Arrangement: Five petals fused at the base and opening into a flared trumpet. Petal lobe length: About 3.1 cm. Petal lobe width: About 1.8 cm. Petal shape: Spatulate. Petal apex: Retuse. Petal margin: Entire. Petal texture, upper and lower surfaces: Smooth, glabrous; satiny; tube, pubescent. Color: Petal, when opening, upper surface: More intense than 74A. Petal, when opening, lower surface: Between 78B and 83A. Petal, fully opened, upper surface: Close to 74A; towards the base and throat, 16A. Petal, fully opened, lower surface: Close to 78B; stripes, 83A.

*Calyx*.—Arrangement: One star-shaped calyx tube with five fused sepals. Sepal length: About 1.8 cm. Sepal width: About 3 mm. Sepal shape: Narroly oblong. Sepal apex: Acute. Sepal base: Cuneate. Sepal margin: Entire. Sepal texture, upper and lower surfaces: Densely pubescent. Color: Immature and mature, upper surface: Towards the apex, 143A; towards the base, 145A. Immature and mature, lower surface: Towards the apex, 143A; towards the base, 145A.

*Peduncles*.—Length: About 4 cm. Diameter: About 1 mm. Angle: About 40° from stem axis. Strength: Moderately strong. Texture: Smooth, glabrous. Color: 145A.

*Reproductive organs*.—Stamens: Quantity/arrangement: Five per flower. Filament length: About 9 mm. Anther shape: Broadly reniform. Anther length: About 1 mm. Anther color: 10B. Pollen amount: Moderate. Pollen color: 10B. Pistils: Quantity: One per flower. Pistil length: About 1 mm. Style length: About 8 mm. Style color: 145A. Stigma shape: Three-lobed, flattened. Stigma color: 145A to 145B. Ovary color: 145C.

*Seed/fruit*.—Seed and fruit development have not been observed on plants of the new *Calibrachoa*.

Garden performance: Plants of the new *Calibrachoa* have been observed to have good garden performance and tolerate wind, rain and temperatures ranging from about 1° C. to about 35° C.

Pathogen/pest resistance: Plants of the new *Calibrachoa* have not been observed to be resistant to pathogens and pests common to *Calibrachoa*.

It is claimed:

1. A new and distinct *Calibrachoa* plant named 'Filindura Pink' as illustrated and described.

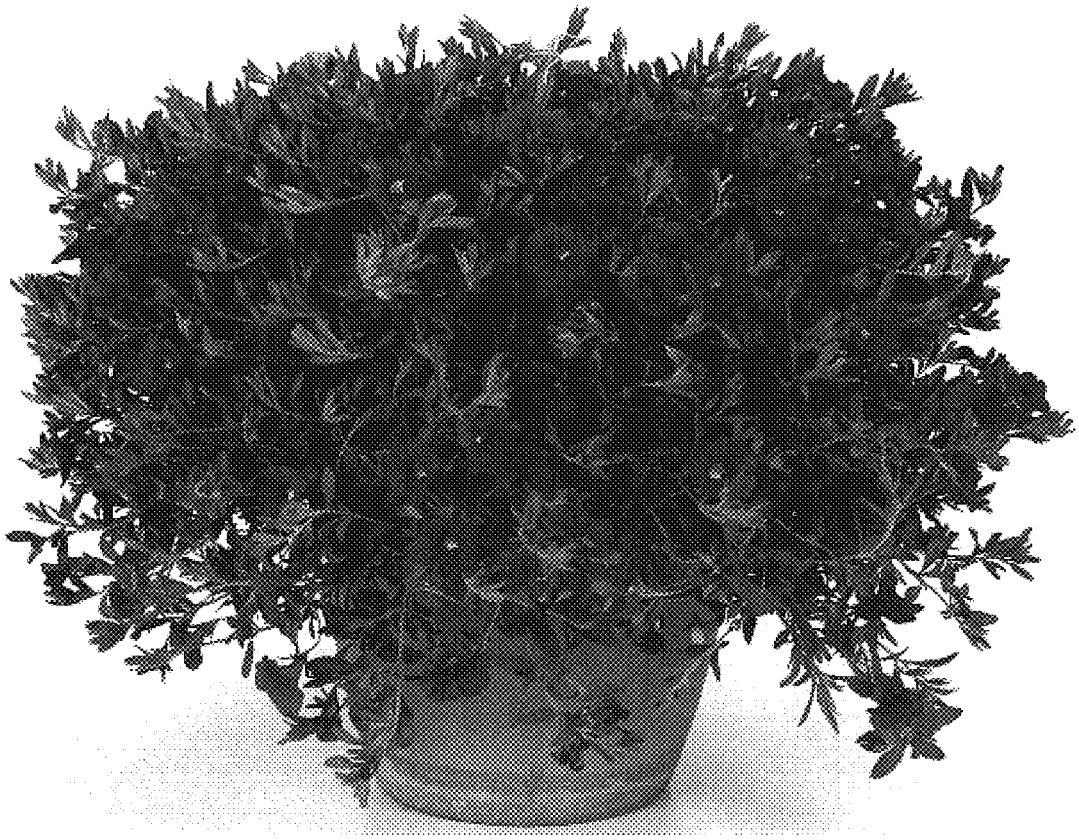

* * * * *